United States Patent
Gomez Duran

(10) Patent No.: US 8,206,439 B2
(45) Date of Patent: Jun. 26, 2012

(54) INTERNAL PROSTHESIS FOR RECONSTRUCTION OF CARDIAC GEOMETRY

(75) Inventor: Carlos Manuel Gomez Duran, Missoula, MT (US)

(73) Assignee: International Heart Institute of Montana Foundation, Missoula, MT (US)

( * ) Notice: Subject to any disclaimer, the term of this patent is extended or adjusted under 35 U.S.C. 154(b) by 1775 days.

(21) Appl. No.: 11/063,236

(22) Filed: Feb. 22, 2005

(65) Prior Publication Data

US 2005/0197696 A1    Sep. 8, 2005

Related U.S. Application Data

(60) Provisional application No. 60/546,872, filed on Feb. 23, 2004.

(51) Int. Cl.
    *A61F 2/24* (2006.01)
(52) U.S. Cl. .................................................. 623/2.37
(58) Field of Classification Search ........ 623/2.36–2.41, 623/2.1; 606/151, 155, 228; 600/16
    See application file for complete search history.

(56) References Cited

U.S. PATENT DOCUMENTS

| | | | |
|---|---|---|---|
| 3,656,185 A | 4/1972 | Carpentier | |
| 4,042,979 A | 8/1977 | Angell | |
| 4,164,046 A | 8/1979 | Cooley | |
| 4,261,342 A * | 4/1981 | Aranguren Duo | 128/898 |
| 4,290,151 A | 9/1981 | Massana | |
| 4,489,446 A | 12/1984 | Reed | |
| 4,602,911 A | 7/1986 | Ahmadi et al. | |
| 5,041,130 A | 8/1991 | Cosgrove et al. | |
| 5,064,431 A | 11/1991 | Gilbertson et al. | |
| 5,415,667 A | 5/1995 | Frater | |
| 5,607,471 A | 3/1997 | Seguin et al. | |
| 5,716,397 A | 2/1998 | Myers | |
| 5,957,977 A * | 9/1999 | Melvin | 623/3.1 |
| 5,972,022 A | 10/1999 | Huxel | |
| 6,074,417 A * | 6/2000 | Peredo | 623/2.1 |
| 6,250,308 B1 | 6/2001 | Cox | |
| 6,332,893 B1 * | 12/2001 | Mortier et al. | 623/2.1 |
| 6,368,348 B1 | 4/2002 | Gabbay | |
| 6,602,288 B1 * | 8/2003 | Cosgrove et al. | 623/2.36 |
| 6,629,534 B1 | 10/2003 | Dell et al. | |
| 6,797,002 B2 * | 9/2004 | Spence et al. | 623/2.38 |
| 6,997,950 B2 * | 2/2006 | Chawla | 623/2.1 |

(Continued)

FOREIGN PATENT DOCUMENTS

FR    2 858 543    2/2005

(Continued)

OTHER PUBLICATIONS http://www.e-echocardiography.com/references/values_tee_values.php, printed Mar. 24, 2009.*

(Continued)

*Primary Examiner* — Thomas J Sweet
*Assistant Examiner* — Cheryl Miller
(74) *Attorney, Agent, or Firm* — Colin L. Fairman; Fulbright & Jaworski

(57) ABSTRACT

Unique semi-circular papillary muscle and annulus bands are described that are useful for modifying the alignment of papillary muscles, a mitral valve annulus and/or a tricuspid valve annulus. Methods to effect the alignment are also described and an unique sizing device that can be used for such alignment is described.

3 Claims, 16 Drawing Sheets

U.S. PATENT DOCUMENTS

| | | | |
|---|---|---|---|
| 7,316,712 B2 * | 1/2008 | Peredo | 623/2.13 |
| 7,347,870 B1 * | 3/2008 | Andrieu et al. | 623/2.36 |
| 2002/0029080 A1 | 3/2002 | Mortier et al. | |
| 2002/0173841 A1 | 11/2002 | Ortiz et al. | |
| 2003/0083742 A1 | 5/2003 | Spence et al. | |
| 2003/0105519 A1 * | 6/2003 | Fasol et al. | 623/2.1 |
| 2003/0130731 A1 | 7/2003 | Vidlund et al. | |
| 2004/0006384 A1 | 1/2004 | McCarthy | |

FOREIGN PATENT DOCUMENTS

| | | |
|---|---|---|
| WO | WO 90/09153 | 8/1990 |
| WO | 01/97741 | 12/2001 |
| WO | WO 01/91667 A2 | 12/2001 |
| WO | 03/037227 | 5/2003 |

OTHER PUBLICATIONS

Axel,Leon "Papillary Muscles Do Not Attach Directly to the Solid Heart Wall", Circulation 2004; 109:3145-3148.* http://www.edwards.com/products/rings/pages/physio.aspx, printed Jan. 19, 2012.*

Pioneer Technologies, Inc., "The Denver-Wells Flexible, Adjustable Annuloplasty Rings", 4 pgs., 1992.

Official Gazette, Apr. 26, 1998, p. 2506, "Annuloplasty and Suture Rings", by John R.M. Write et al.

"Surgical Techniques for the Repair of Anterior Mitral Leaflet Prolapse", by Carlos M.G. Duran, M.D., Ph.D., *J. Card Surg*, 1999; 14: pp. 471-481.

"Editorial: Distribution of Chordae Tendinae Tension in the Porcine Mitral Valve", by Carlos M.G. Duran, *The Journal of Heart Valve Disease*, vol. 11, No. 3, pp. 335-336, May 2002.

"Chordal-sparing mitral valve replacement: pitfalls and techniques to prevent complications", by Hideki Sasaki, Kenji lhashi, *European Journal of Cardio-thoracic Surgery*, 24 (2003) pp. 650-652.

"Simplified chordal reconstruction: 'oblique' placement of artificial chordae tendineae in mitral valve replacement", by Yoshiharu Soga, et al., *European Journal of Cardio-thoracic Surgery*, 24 (2003) pp. 653-655.

"Surgical Repair of the Prolapsing Anterior Leaflet in Degenerative Mitral Valve Disease", by Gebrine El Khoury, et al., *The Journal of Heart Valve Disease*, vol. 9, No. 1, pp. 75-81, Jan. 2000.

"Papillary Muscle Sling: A New Functional Approach to Mitral Repair in Patients With Ischemic Left Ventricular Dysfunction and Functional Mitral Regugitation", by Ulrik Hvass, MD., et al., *Ann Thorac Surg*, 2003; 75, pp. 809-811.

"Atrioventricular Plane Displacement and Left Ventricular Function", by Mahbubul Alam, MD, PhD and Gunnar Rosenhamer, MD, PhD., *Journal of the American Society of Echocardiography*, 1992, vol. 5, No. 4, pp. 427-433.

"Nondestructive Analysis of Mitral Valve Collagen Fiber Orientation", by R.P. Cochran et al., *American Society for Artificial Internal Organs Transactions*, 1991, vol. 37, No. 3, pp. M447-M448.

"Conservative operation for mitral insufficiency", by Carlos G. Duran, M.D., Ph.D., et al., *Journal Thoracic and Cardiovascular Surgery*, 1980, vol. 79, pp. 326-337.

"A Revised Terminology for Recording Surgical Findings of the Mitral Valve", by Naresh Kumar, et al., *The Journal of Heart Valve Disease*, 1995, vol. 4, No. 1, pp. 70-75.

"The Heart as a Suction Pump", by Thomas F. Robinson, et al., *Scientific American*, 1986, vol. 254, No. 6, pp. 84-91.

"Mitral Valve Anatomy and Morphology: Relevance to Mitral Valve Replacement and Valve Reconstruction", by Gerda L. van Rijk-Zwikker, M.D. et al., *Journal of Cardiac Surgery*, 1994, vol. 9 (Suppl), No. 2, pp. 255-261.

International Search Report PEP 10 18 4773 dated Apr. 20, 2012 (1 pg.).

Hvass, Ulrik, et al, "Papillary Muscle Sling: A New Functional Approach to Mitral Repair in Patients with Ischemic Left Ventricular Dysfunction and Functional Mitral Regurgitation," The Annals of Thoracic Surgery, Elsevier, US, vol. 75, No. 3, Mar. 1, 2003, pp. 809-811.

* cited by examiner

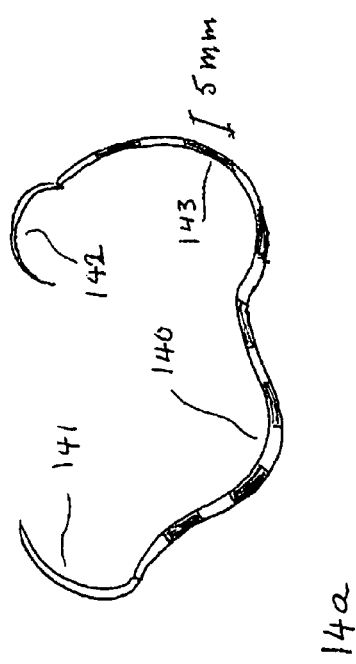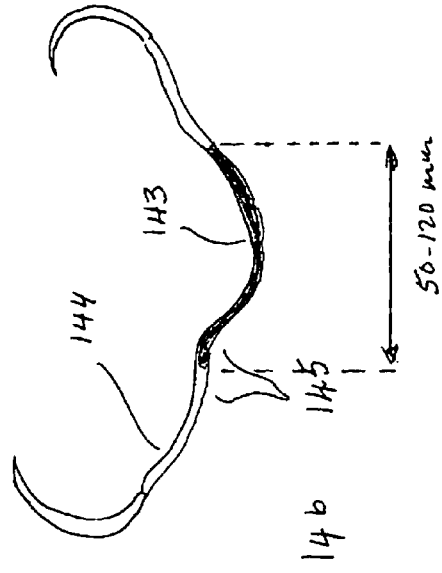
FIGURE 14

INTERNAL PROSTHESIS FOR RECONSTRUCTION OF CARDIAC GEOMETRY

CROSS REFERENCE TO RELATED APPLICATION

This application claims benefit under 35 U.S.C. §119(e) to application Ser. No. 60/546,872, entitled "Novel System for Restoration of the Failing Heart" by Carlos, M. G. Duran on Feb. 23, 2004, the contents of which are incorporated herein in their entirety.

FIELD OF THE INVENTION

The present invention relates to heart surgery and to the treatment of congestive heart failure.

BACKGROUND OF THE INVENTION

The heart has four chambers, the left and right atria and the left and right ventricles. The atria collect blood as it returns from the body in the case of the right atrium or from the lungs in the case of the left atrium. During diastole the atrioventricular valves (tricuspid valve on the right side and mitral on the left) open, filling the ventricles. During systole the ventricles contract closing the atrioventricular valves and expelling the blood towards either the body (left) or the lungs (right).

The bicuspid or mitral valve is located in the left atrioventricular opening of the heart. It is encircled by an annulus and consists of two valve leaflets of unequal size. The larger valve leaflet (called ventral or anterior cusp) is adjacent the aortic opening. The smaller leaflet is the dorsal or posterior cusp. The leaflets are composed of strong fibrous tissue which is thick in the central part but thin and translucent near the margin. The valves are constructed so as to pass blood unidirectionally from the left atrium to the left ventricle of the heart.

The tricuspid valve is located in the right atrioventricular opening and comprises three leaflets referred to as the anterior, posterior and septal cusps. The leaflets are roughly quadrangular in shape and attached to an annulus.

Both the mitral and tricuspid valves, also called a trioventricular valves, prevent regurgitation of blood from the ventricle into the atrium when the ventricle contracts. In order to withstand the substantial back pressure and prevent regurgitation of blood into the atrium during the ventricular contraction, the cusps are held in place by delicate chords which anchor the valve cusps to papillary muscles of the heart. These chords are of two types according to their insertion into the leaflet's free edge ("marginal chords") or the body of the leaflet ("basal chords"). Among the basal chords there are two anterior and two posterior particularly thick and strong chords called "stay chords".

In heart failure valve regurgitation often occurs due to dilatation of the valve annulus. When the leaflets fail to close completely during ventricular systole all the leaflet chords are under abnormal tension. The result of valve regurgitation is often associated with arrhythmias, chest pain, cardiac dyspnea, and other adverse clinical symptoms.

In heart failure, there is an apico-lateral displacement of the papillary muscles due to the increase in sphericity of the ventricles. This papillary muscle displacement pulls o the stay chords which in turn pulls the body of the leaflets towards the apex of the ventricle. This distortion of the valve geometry increases the mechanical stress of the myocardial fibers initiating a downward spiral of the ventricular contractility.

Therefore, a need exists for correction of distorted valve geometry by novel surgical techniques and devices.

BRIEF SUMMARY OF THE INVENTION

The present invention provides a unique unexpectedly simple and easy to use cardiac prosthesis that includes a semi-circular band portion having first and second ends. The first end includes a first portion of a tether and the second end includes a second portion of the tether, such that when the first and second portions of the tether are secured to each other, the ultimate assembly provides an adjustable semi-circular band. This band can be affixed to an annulus of a valve, or can be inserted through trabeculae associated with papillary muscles.

The cardiac prosthesis band can be in the form of a tube or a unitary rod. The two portions of the tether are affixed to the ends of the band.

In one embodiment, the band can be hollow, such that the tether can extend through the band, such that the band acts as a cover to the tether itself. The tether in this embodiment include a first and second end that engage each other, such as a quick tie or a suture.

The cardiac prosthesis is formed from a biocompatible material. Suitable biocompatible materials include those known in the medical arts such as Dacron, teflon, polyurethanes, nylons, polyesters, silastic, nitinol, nitinol mesh, titanium and titanium mesh or tissues such as pericardium or other biologic membranes.

The invention further provides methods to align the papillary muscles of a ventricle and the stay chords so that valve regurgitation, is reduced or eliminated. This is accomplished by forming a passage about the papillary muscles of the ventricle and surrounding trabeculae. The cardiac prosthesis of the invention, as described throughout the specification is guided through and adjusted via the tether, such that the papillary muscles and chords are aligned relative to the valve annulus. In an alternative embodiment, the cardiac prosthetic can be guided through the trabeculae simultaneously while forming the passage, or the device can be configured such that a needle or hook is attached to either end of the tether and then removed prior to securing the tether.

The method of the invention can further include securing an annuloplasty prosthesis about the annulus of the valve adjacent to the papillary muscles. Annuloplasty prosthesis are known in the art and the invention contemplates that any of such devices can be used in combination with the present invention. Alternatively, a second cardiac prosthesis of the invention can be used as the annuloplasty prosthesis.

The method of the invention can further include securing synthetic or biologic chords from the papillary muscle to the annuloplasty prosthesis. There are several ways to accomplish this. The chords can be inserted through tissue about each prosthesis. Additional securing can be accomplished by use of pledgets to help prevent damage to the tissue. Alternatively, the replacement chords can be inserted through each prosthesis, thereby minimizing potential damage to the surrounding tissue. The chords can be made of materials known in the art, such as nylons, polypropylene, polyesters, polyurethanes and the like or made of biologic membranes. The replacement chord can also be a rigid rod. In any event, the synthetic chords will have a length wherein the relationship between the lengths of the chords are adjusted such that the distance from the tips of the papillary muscles is approximately equal to the intertrigonal distance of the valve annulus.

Generally, two or more replacement chords are secured, as described above, from each papillary muscle or papillary (cardiac) prosthesis to the annuloplasty prosthesis. The replacement chord can be attached at a point near the appropriate trigone.

To help estimate the intertrigonal distance and assist with the methods of the invention, the present invention also provides a trigonal-papillary sizing device. The trigonal-papillary sizing device includes a handle attached to a two forked prong. The two forked prong includes a proximal portion and two distal ends each having an equivalent length, wherein the proximal portion connects the two prongs. The two distal prong ends are generally rounded or configured in such a fashion as to not damage tissue as the device is being manipulated in the ventricular chamber. The distance between the two prongs and the lengths of the two prongs are equivalent, the distances being equal to the intertrigonal distance of the valve. Sizing devices can be constructed such that the operator can quickly choose the appropriate size by comparing the distance between the forks with the intertrigonal distance. The present invention, therefore provides, intertrigonal-papillary sizing devices of varying dimensions that are suited to various sized hearts.

In one embodiment, the two prongs of the trigonal-papillary sizing device form a single planar unitary structure. In another embodiment, the single planar unitary structure curves out of the plane formed by the prongs, much like a chisel. In one aspect, the sizer is formed of a transparent material so that the operator can visualize the papillary muscles, ventricle and chords during the procedure.

The present invention also provides methods to align the papillary muscles of the ventricle. This is accomplished by forming a passage about the papillary muscles of the ventricle through the surrounding trabeculae. The cardiac prosthesis of the invention, as described throughout the specification, is guided through and adjusted via the tether, such that the papillary muscles and chords are aligned relative to the mitral valve annulus. In an alternative embodiment, the cardiac prosthetic can be guided through the trabeculae simultaneously while forming the passage, or the device can be configured such that a needle or hook is attached to either end of the tether and then removed prior to securing the tether. Optionally a biocompatible tape, such as Gore-Tex could be used. Additionally, pledgets can be secured to the papillary muscles with the suture or tape to prevent damage to the papillary tissue.

The distance between the trigones is measured, optionally, with a trigonal-papillary sizing device as described herein. The trigonal-papillary sizing device has a horizontal member and two vertical members of equal length attached to the distal ends of the horizontal member such that the vertical members have the same length as the horizontal member, wherein the horizontal member has a length equivalent to the intertrigonal distance.

The cardiac prosthesis is adjusted via the tether, such that the papillary muscles and ventricular chords are aligned relative to the intertrigonal distance.

The method can further include securing an annuloplasty prosthesis about the mitral valve annulus adjacent to the papillary muscles. Annuloplasty prosthesis known in the art can be used and the invention contemplates that any of such devices can be used in combination with the present invention. Alternatively, a second cardiac prosthesis of the invention can be used as the annuloplasty prosthesis.

The method can further include securing chords from the cardiac prosthesis to the mitral valve annuloplasty prosthesis. There are several ways to accomplish this. The chords can be inserted through tissue about each prosthesis. Additional securing can be accomplished by use of pledgets to help prevent damage to the tissue. Alternatively, the chords can be inserted through each prosthesis, thereby minimizing potential damage to the surrounding tissue. The chords can be made of materials known in the art, such as nylons, polypropylene, polyesters, polyurethanes and the like or biologic membrane. The chord can also be a rigid rod. In any event, the chords will have a length wherein the relationship between the lengths of the chords are adjusted such that the distance from the tips of the papillary muscles is equal to the intertrigonal distance of the mitral valve annulus.

Generally, two or more replacement chords are secured, as described above, from each papillary muscle or cardiac prosthesis to the annuloplasty prosthesis. The replacement chord can be attached at a point near the appropriate trigone.

The present invention further provides packaged kits that include the cardiac prosthetic of the invention, and optionally, a second cardiac prosthesis, or an annuloplasty prosthesis and, optionally, a sizing device, and instruction how to locate one or more of the prosthesis as described herein.

BRIEF DESCRIPTION OF THE FIGURES

FIG. 14 is a view of color coded suture to be used as neo-stay chords.

DETAILED DESCRIPTION

Figure 1:
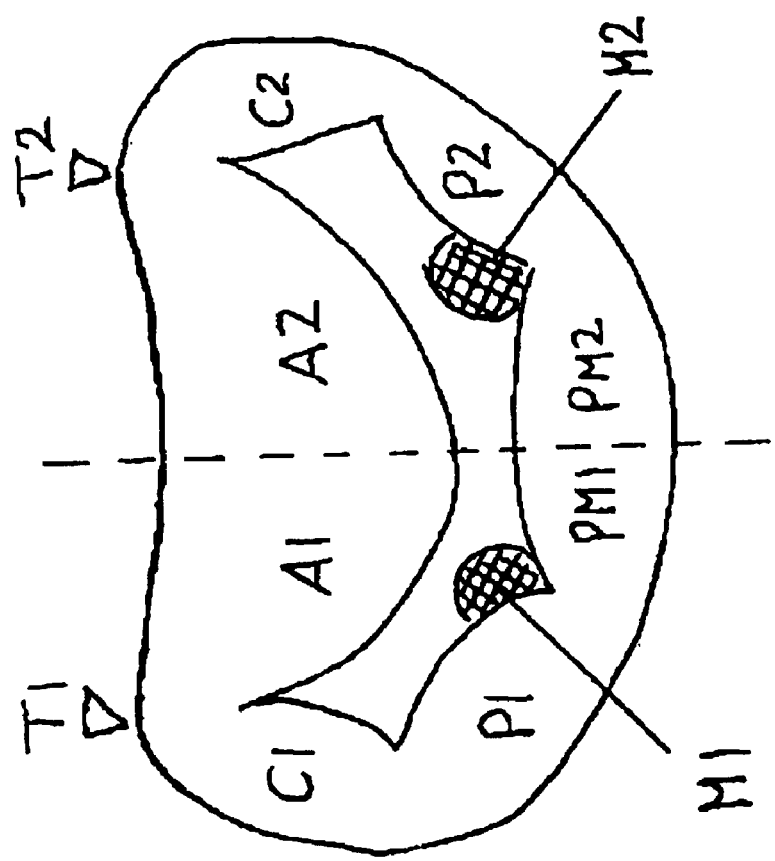
FIG. 1 depicts an operator's view of the mitral valve in the closed position as seen from the open left atrium.

In congestive heart failure the dimensions of the mitral apparatus are severely altered. 1) The whole mitral annulus is dilated but non homogeneously. This dilatation includes the intertrigonal distance and posterior annulus but is particularly severe in its antero-posterior diameter. This dilatation reduces the leaflet coaptation generating mitral regurgitation. 2) The papillary muscles are displaced laterally and apically tethering the leaflets and consequently reducing their mobility and increasing the valve regurgitation. 3) The papillary displacement also pulls on the basal stay chords deforming the anterior leaflet.

The present invention, therefore, provides for the complete internal reconstruction of the mitral apparatus and includes a mitral annuloplasty, a papillary plasty and the implantation of new stay chords that brings closer the papillary muscles to the trigones of the mitral annulus. These aims require not only suitable devices but also guidelines easy to use by the surgeon to select the appropriate dimensions specific for each patient.

The novel system described in the present invention provides these dimensions based on the theoretical normal intertrigonal distance for the patient. It has been presently discovered that there is a constant ratio (0.8) between the aortic valve annulus diameter (normal in these patients) and the normal intertrigonal distance. In the normal heart, the distances between papillary muscles and between papillary muscles and both mitral trigones are similar to the intertrigonal distance. Therefore, once the aortic annulus diameter of the individual patient (easily available with echocardiography) is discerned, the surgeon has a template for restoring the normal geometry of the whole mitral apparatus. The present invention provides unique unexpectedly simple and easy to use devices and methods to treat heart deformities described herein. The discovery that there is a relationship between the intertrigonal distance and the distance between papillary muscles and the distance between papillary muscles and trigones provides a reliable method to correct for valve regurgitation. The present invention exploits this discovery in terms of methods to correct the prolapsed area as well as by providing prosthetics useful in correcting the abnormalities.

The present invention provides: 1) a method for the complete reconstruction of the entire mitral apparatus; 2) a method to determine the correct dimensions of the mitral apparatus in the individual patient; 3) an instrument for determining at the time of surgery, the appropriate dimensions to aim for by the surgeon; 4) a mitral annuloplasty device specific for the treatment of patients with ischemic and dilated cardiomyopathies; 5) a specific device designed for the relocation of the papillary muscles and 6) the application of these devices to the geometric reconstruction of the tricuspid valve.

Heart Failure represents a major health problem. The main causes of heart failure are a heart muscle disease leading to a dilated heart ("Dilated Cardiomyopathy"), a previous myocardial infarction ("Ischemic cardiomyopathy") or a long-standing valve insufficiency. Regardless of the initiating insult, the heart compensates with a number of adaptative mechanisms to maintain adequate cardiac output necessary to maintain organ perfusion. The chronic effect of these compensatory changes results in changes in the geometry of the left (or right) ventricle called remodeling. These changes lead to an abnormal geometry of an otherwise normal mitral and tricuspid valves that result in what is known as "functional" mitral/tricuspid incompetence.

The present invention is directed toward restoring the distorted anatomic relationships between papillary muscles, valve annulus and distance between papillary muscles and annulus. It consists of the implantation of a mitral and/or tricuspid annuloplasty ring, a papillary muscle band (a cardiac prosthesis) and several new artificial basal chords. Based on in vivo and in vitro anatomic studies in human and animals a system to determine the selection of the appropriate sizes of each device for each individual patient has been developed. An instrument has been designed to determine the correct implantation of the above devices.

Most of our understanding of the function of the heart is based on experiments performed in vitro with isolated hearts or myocardial fibers. Recent technological improvements have made possible a more precise and closer to normal, in vivo measurements that question our established views giving rise to a radically different understanding of the heart's function as a pump. Robinson, Factor and Sonnenblick (1) in a publication entitled "The Heart as a Suction Pump" have proposed a completely different explanation of the cardiac pump mechanism. Because of its relevance to the present invention, the following paragraphs are an attempt at describing this new approach.

The human heart has four chambers, the left and right atria and the left and right ventricles. The atria collect blood as it returns from the body in the case of the right atrium or from the lungs in the case of the left atrium. During diastole the atrioventricular valves (tricuspid valve on the right side and mitral on the left) open, filling the ventricles. During systole the ventricles contract closing the atrioventricular valves and expelling the blood towards either the body (left) or the lungs (right). Present day understanding of the function of the heart stems from the work performed in the 19th century by Otto Frank in Germany and Ernest Starling in England. According to the Frank-Starling law, the energy imparted to the blood by the systolic contraction of the ventricles is proportional to the length of the ventricular muscle fibers at the end of the preceding diastole. Once systolic contraction is complete the subsequent diastolic filling is a passive function of venous pressure, which stretches the relaxed ventricular muscle: This principle has dominated the thinking of most cardiologists and surgeons.

Not to be limited by theory, it is believed according to Robinson and associates, the dynamic relation between systole and diastole is critical for the proper action of the heart. When the heart contracts, it propels blood upward and thereby, in accordance with Newton's law of action and reaction, propels itself downward. This recoil stretches the great elastic vessels and connective tissue that hold the heart in place. As the heart subsequently relaxes it springs upward, meeting the flow of blood head on. These authors propose that the systolic contraction compresses the elastic elements of the muscle fibers in such a way that at the end of systole, even without any external filling the natural tendency of the ventricles is to expand. This expansion creates a negative pressure, or suction, that pulls blood from the atria to the ventricles. During systole the base of the heart moves away from the head stretching the compliant connective tissues and blood vessels that hold it in place. These connecting tissues convert a fraction of the heart's kinetic energy of stretching and exert an upward force on the base, which is drawn back toward the head during diastole.

Mitral Valve Anatomy

The mitral valve is a one-way valve located between the left atrium and left ventricle. Traditionally it has been described as formed by a large anterior leaflet and a smaller posterior leaflet separated by a cleft called "commissures". More detailed observation has shown that the commissures are in fact, small leaflets and that the posterior leaflet has most often two clefts that divide the posterior leaflet into three scallops: two lateral and one medial. Therefore practically, the mitral valve has six leaflets of different sizes. The leaflets are inserted peripherally into the atrioventricular junction also called "mitral annulus". The mitral annulus is a complete ring of fibrous tissue in only 10% of cases, the remaining 90% of cases has an incomplete fibrous annulus. In all cases there are two very strong fibrous nodules situated at the extremities of the base of the anterior leaflet or "aortic curtain". Both extremities of the aortic curtain are therefore anchored into the very strong right and left "trigones" which are the main constituents of the fibrous skeleton of the heart. Medially, the leaflets end in a "free edge" or coaptation area, because during systole they come in contact with each other ensuring an efficient closure of the mitral valve. To avoid leaflet prolapse into the left atrium while the pressure in the left ventricle is much higher than in the atrium, the free edge of the leaflets is held with numerous string-like "chordae tendineae" that are attached at their other extremity to the left ventricular wall through two "papillary muscles".

Mitral Valve Terminology

Because there have been numerous studies on the anatomy of the mitral valve performed by anatomists, cardiologists and cardiac surgeons different terminologies have been used contributing to a considerable confusion. The exponential popularity of mitral valve repair that involves numerous surgical maneuvers at different levels of the valve demanded a standard surgical nomenclature that would improve communication among surgeons and echocardiographers.

To clarify this issue a simple terminology was developed to describe the anatomic, echocardiographic and surgical findings (2). This terminology is based on the surgical i.e. atrial view of the valve. All anterior structures are identified with the letter A and those posterior with the letter P. Those structures supported by the anterior papillary muscle and situated to the left of the surgeon, are identified with the numeral 1 and those supported by the posterior papillary muscle (and to the right of the surgeon) with the numeral 2. The two papillary muscles are therefore termed M1 (to the left of the surgeon) and M2 (to the right of the surgeon). The two fibrous trigones are called T1 and T2. The anterior leaflet is divided into A1 and A2 according to the insertion of their chords into either papillary muscle (M1 or M2). The commissural areas are identified as C1 and C2. The two lateral scallops of the posterior leaflet are called P1 and P2. The mid scallop (PM) is divided again according to the origin of its chords from the papillary muscles into PM1 and PM2. All chords are identified by their origin from the papillary muscles and insertion into the corresponding leaflet.

The Mitral Subvalvar Apparatus

In an attempt to introduce order into the apparent variability of the over two dozen chords, most authors divide them into three groups according to their points of origin and insertion. First order chords or "marginal" chords are those that arising from a papillary muscle are inserted into the free margin of the corresponding leaflet. Second order or "basal" chords also arise from the papillary muscles but are inserted into the undersurface or ventricular aspect of the leaflets. Third order chords, only present in the posterior leaflet, arise from the ventricular wall and are inserted into the undersurface of the posterior leaflet.

Among the basal chords, there are usually four particularly strong and thick tendon-like "principal" or "strut" chords. Arising from each papillary muscle, two anterior and two posterior strut chords are inserted into the undersurface of the corresponding leaflet. The strut chords of the anterior leaflet are inserted into the "aortic curtain" near the anterior part of the mitral annulus. Because of their importance and function as support of the central structure of the heart, they are referred to as "stay chords" and according to present terminology, S1 and S2. Posterior stay chords are more variable but usually are inserted at the base of the mid-scallop (PM) of the posterior leaflet close to the clefts with P1 and P2.

The function of the marginal or first order chords is to maintain leaflet apposition during valve closure. Not to be limited by theory, the function of the basal chords has been assumed to be of support of the belly of the anterior leaflet but being thicker than the marginal chords suggests a more significant purpose. This is particularly evident for the two very thick anterior stay chords. Van Zwikker et al. (3) showed in an isolated perfused pig heart, the presence of two anterior basal chords that remained tense during the whole cardiac cycle suggesting they might play an important role in maintaining left ventricular geometry. The anterior stay chords can be easily identified by transthoracic echocardiography in the left parasternal long axis view. Their length in the human, average 1.86±0.43 mm with a thickness of 1.24±0.51 mm. An echocardiographic study has shown that both anterior stay chords remain under tension and with constant length during the whole cardiac cycle. Also, the behavior of the normal mitral valve in an acute ovine model with implantation of small (1 mm) transducer crystals was studied. Under stable hemodynamic conditions, geometric changes were time related to simultaneous LV and aortic pressures. The results showed that from mid diastole to end systole the mitral annulus area contracted by −16.1±1.9% (mean±SEM). The mitral annulus deformation was heterogeneous. The anterior mitral annulus expanded (T1-T2: +11.5±2.3%) while the posterior mitral annulus contracted in systole (P1-P2: −12.1±1.5%). The distance between papillary muscle tips and trigones did not change during the cardiac cycle. This distance has now been shown to remain constant even during acute coronary balloon occlusion that otherwise induced large changes in the size and shape of the mitral annulus. Studies in sheep have shown that geometrical changes consist of a posterior papillary muscle shift away from the anterior mitral annulus inducing tethering of the leaflets and mitral regurgitation (4). Similar changes in the tricuspid valve have now been demonstrated within the scope of the present invention.

Cochran and associates (5) in a study of the distribution and direction of the collagen fibers in the anterior mitral valve leaflet, have shown that the fibers are oriented from the region of insertion of the stay chords towards the fibrous trigones. The present invention accounts for the direction and magnitude of stress directed from the papillary muscle through the stay chords into the fibrous trigones and through echocardiography of normal humans, that the stay chords are in a plane that stretches from the papillary muscle tips to the aortic curtain and ascending aorta including the fibrous trigones.

Left Ventricular Pumping (LV) and the Atrio-Ventricular Plane Displacement

Assessment of LV systolic function requires knowledge of the pumping action of the ventricle. LV pump function is frequently described as mainly being the effect of the contraction of circumferential fibers. Recent studies however, point out the importance of the longitudinal myocardial fibers. While the outer cardiac silhouette changes very little during the cardiac cycle, the major changes occur intracardially as a result of the movements of the atrioventricular (AV) plane. The observation that the epicardial site of the apex remains immobile during the entire cardiac cycle reinforces this notion.

Alam and Rosenhamer (6) suggest that this way of pumping the blood without much displacement of the intrathoracic structures surrounding the heart should be physiologically useful in minimizing the heart's energy expenditure during the cardiac cycle. During systole the base of the left ventricle moves toward the apex. The descent of the atrioventricular plane begins during the isovolumic contraction and continues to the completion of ejection when the major displacement occurs. In healthy human subjects these authors found with M-mode two and four chamber views, a displacement of the AV plane of 14-15 mm during systole. After acute myocardial infarction this displacement was significantly reduced in both anterior and inferior infarcts. All these measurements were taken from a virtual plane extending from the top of the septum to the lateral aspect of the mitral annulus. These two points that according to the above studies correspond to the a trioventricular plane are in fact, not an anatomical plane since the base of the LV is formed by the aortic and mitral valves which are not in the same anatomic plane. In fact, the base of the aortic valve and the mitral annulus are in different planes. Both these planes hinge at the base of the aortic curtain or intertrigonal distance, common to both valves. The planes of the aortic and of the mitral valves form an obtuse angle called the "mitro-aortic angle". In normal individuals this angle changes very little during the cardiac cycle.

As seen above, when the heart contracts (like a squid in the water) it drives blood upwards while the heart moves downwards. This systolic contraction stretches the great vessels and connective tissue attached to the base of the heart (atrioventricular plane), which pull in the opposite direction with their elastic force. In this way a fraction of the heart's kinetic energy is converted into stretching energy and exert an upward force on the base, which is drawn back toward the great vessels during subsequent relaxation in diastole. The heart is a suction pump. During early diastole, the expanding heart moves upwards toward the incoming blood under the influence of the great vessels elastic recoil force. This upward motion creates a negative pressure and suction that raises the velocity of the blood filling the ventricle. For any given heart the suction is greatest when the size of the heart at end-systole is least. The recoil mechanism of the great vessels on the atrioventricular plane contributes greatly to the early filling of the left ventricle in diastole increasing the efficiency of the pump mechanism by applying the energy of systole to power diastole. In heart failure, the ventricle does not contract completely in systole increasing in diastole the remaining blood volume in the ventricle. The normal elastic energy is therefore not stored during systole and cannot be released as recoil during diastole. It has been found that an average force of 178N is required to pull the aortic root from its diastolic position 10 mm towards the apex. This elastic force of the aorta pulls on the atrioventricular plane (represented by the fibrous trigones) in the opposite direction to the systolic descending movement of the atrioventricular plane. This should result in a narrowing of the mitro-aortic angle. In a videofluoroscopic study in sheep and in an echocardiographic study in humans it has been shown, that the mitro-aortic angle only changes on average 2 degrees during the whole cardiac cycle.

The apex of the heart does not move and the great vessels are held by connective tissue. Therefore the movements of the heart during the cardiac cycle must occur between these two fixed points. Also, the silhouette of the heart does not change significantly during the cardiac cycle. Systole consists in a downward movement of the base of the heart that results in thickening of the ventricular wall and reduction of its cavity. During diastole the base returns to its previous position due to the elastic recoil stored in the great vessels. Therefore, cardiac function is basically a seesaw movement of the atrioventricular plane. This virtual plane is formed by the plane of the base of the aortic valve and the plane of the mitral valve orifice. These two planes are at an angle or mitro-aortic angle. This angle only varies a few degrees during the cardiac cycle. The apex of this angle corresponds to the hinge of the base of the anterior mitral leaflet or aortic curtain with its extremities anchored to both trigones of the fibrous skeleton of the heart. The only anatomical structures that connect the ascending aorta to the apex of the heart are the anterior mitral valve basal chords we have labeled as stay chords. The papillary muscles, stay chords, trigones and ascending aorta are in a straight line. During the cardiac cycle, the apex of the mitro-aortic angle requires a structure that counteracts the pulling force of the ascending aorta. The stay chords because they connect the papillary muscles to the trigones (through the aortic curtain), pull down the center of the atrioventricular plane against the force of the ascending aorta, keeping the mitro-aortic angle constant and thus maintaining the pumping mechanism of the heart. This mechanism explains the well-known decrease in stroke volume that follows surgical transection of the chordae tendineae when performing a complete mitral valve replacement.

In heart failure, the lateral displacement of the papillary muscles pulls the stay chords which in turn pulls the mitral leaflets towards the apex of the left ventricle. This distortion of the mitral geometry increases the mechanical stress of the myocardial fibers initiating a downward spiral of the ventricular contractility. Based on the above data, the present invention consists in the surgical restoration of the central structure of the heart. This procedure includes specific devices and methods, as described herein, to select the appropriate distances and sizes to restore the normal geometry in each individual patient.

Atrio-Ventricular Valve Annuloplasty Device

In one embodiment of the methods of the invention, the dilated mitral/tricuspid annuli should be reduced with an appropriately sized annuloplasty device. Although there are several types of rings and bands available in the market, none has been specifically designed to be used in cases of heart failure.

The present invention provides methods based, in part, that the aortic and mitral valves have in common the aortic curtain that hangs from both trigones. The aortic valve base diameter can be easily measured by echocardiography. The present invention accounts for the relationship in human and animal hearts that there is a constant ratio between the normal aortic valve annulus diameter and the intertrigonal distance. This relationship is 0.8 of the aortic diameter. Therefore, the surgeon can determine before opening the heart, the size of the intertrigonal distance which is used to select the appropriate annuloplasty device size.

Although any known annuloplasty device can be used for the purpose of reducing the size of the mitral annulus in cases of mitral disease, none has been specifically designed for the treatment of heart failure. The present invention contemplates the construction of such a band. This device can be made semi flexible or totally flexible with synthetic or biologic biocompatible materials or with alternative rigid and flexible sections. Also the ring can be made as a band of biocompatible materials that is joined with a string or wire so that the device becomes a complete ring. Also this member that joins the extremities of the band can be made so that it can be disconnected from the band so that the ring can be open. The joining mechanism, a tether, between the band and the string can be a knot, hook, clasp or other joining mechanisms well known in the art. This joining mechanism can also be made so that it has a kind of ratchet that allows to increase or decrease the length of the string and therefore the total length of the complete ring.

Besides the tether that connects the two extremities of the band making it a ring (or a complete ring), the band can have another independent string that can join two parts of the band so that once the band has been sutured to the mitral annulus (or tricuspid), this string can reduce the diameter of the orifice at a particular point, i.e. the mitral orifice will be deformed selectively at this point by deforming the ring by reducing the distance between two selected points of the ring. This model is particularly designed to reduce selectively the antero-posterior diameter of the ring following recent evidence that in ischemic mitral regurgitation, the annulus dilatation is non homogeneous but more significant in its antero-posterior diameter (9) Alternatively, a ring holder can be constructed with a handle that by turning it, the length of the string that joins the extremities of the band can be controlled.

The band can be equivalent to the papillary semi-circular band; it consists of a flexible or semi flexible tubular band, between about 1.5 and about 6 mm, e.g., about 3 mm in diameter and length between ±50 mm and 100 mm. It can be constructed with biologic or biocompatible materials as described herein. The distal ends of the band are joined with a tether, as described herein, that in one embodiment can be a suture, string or tape with a length approximately one third of the length of the band. This band can be completely flexible or have incorporated rigid segments of different lengths which can be placed in different locations. Alternatively, these rigid segments can be incorporated within the standard Flexible Duran Ring.

As described above, the semi-circular band has a tether that can be secured once the band has been sutured to the mitral or tricuspid annulus. A variety of methods for joining the ends of the tether are known in the art and are described throughout the specification. This type of ring provides the ability to adjust the perimeter of the mitral or tricuspid annulus at will.

In another configuration, a single flexible member is placed within the tubular semi-circular band and protrudes at both extremities of the band so that the overall reduction in the annuloplasty perimeter is not limited to the intertrigonal distance but to the whole semi-circular band. In order to observe the degree of constriction of the resultant ring, both extremities of the protruding tether can be passed through a tourniquet. Also, both flexible members can be passed through an instrument that when rotated, brings the two ends of the tether closer together. Furthermore, the two extremities of the tether can cross the left atrial wall and be placed within a tourniquet outside the heart. This model allows to constrict the ring under echocardiographic control while the heart is beating.

In still another embodiment, the present invention includes the addition of a string designed to selectively change the shape of the annuloplasty band and more specifically, reduce the abnormal antero-posterior dilatation of the ischemic mitral or tricuspid orifice. In a first configuration, a double ended suture is anchored to the extremity of the semi-circular band at the level of the right trigone. This single or double string crosses the valve orifice and is inserted in the opposing part of the band. Tying the string brings the posterior annulus closer to the right trigone. In a second embodiment one string is anchored to the band at the level of the right trigone. A second string is anchored within the band at the opposite point. This string runs within the right half of the band and emerges close to the other string at the level of the right trigone. Drawing on both strings will reduce not only the antero-posterior diameter of the annulus but also reduces the right half of the orifice. As in the above description, the two strings can be passed through a tourniquet to allow the surgeon to check the degree of annulus deformation.

Papillary Muscle Band

The papillary muscle heads should be correctly repositioned (relative to the trigones) with an appropriate device (papilloplasty). Although papilloplasty can be achieved with sutures that bring the papillary muscles heads closer together, a simpler and more efficient method is to implant a specially designed band (a cardiac prosthesis).

The cardiac prosthesis, i.e., a papillary muscle band, of the invention generally includes a semi-circular band portion generally having first and second ends. The first end includes a first portion of a tether and the second end includes a second portion of the tether, such that when the first and second portions of the tether are secured to each other, the ultimate assembly provides an adjustable semi-circular band that forms a ring. This band can be affixed to an annulus of a valve, or can be inserted through trabeculae associated with papillary muscles.

The term "tether" as used herein refers to a material that is suitable to connect the two distal ends of the semi-circular band. The two portions of the tether can be integrally affixed to the two distal ends of the semi-circular band or can be removably affixed as known in the art. Suitable tethers include, for example, sutures, a quick connect assembly, a tourniquet (to secure sutures or tape affixed to the semi-circular band), a hook and eye assembly, a clasp, a threaded screw, a staple, a quick connect, Velcro®, a button mechanism, and those methods to secure ends of two adjacent members known in the medical arts.

The cardiac prosthesis band can be in the form of a tube or a unitary rod. The two portions of the tether are affixed to the ends of the band.

In one embodiment, the band can be hollow, such that the tether can extend through the band, such that the band acts as a cover to the tether itself. The tether in this embodiment include a first and second end that engage each other, such as a quick tie or a suture.

The band should be flexible in order to adapt to the continuous movements of the papillary muscles during the cardiac cycle. A thin, 1-2 mm inner core of silastic rubber or suture material well known in the art, can be placed in the interior to give some body to the band. Also a radiopaque salt (e.g. barium sulphate) can be added to make it radiological visible. The overall thickness of the band should be between about 1.5 to about 6 mm, e.g., 3 mm. Different sizes of semi-circular band are required to be selected according to the patient's size. Indicative total lengths of the band should be between 50 mm and 100 mm although other lengths can be manufactured. A marker (with colored suture) can be placed on the band at its center. These devices can be used to realign the mitral valve papillary or tricuspid valve papillary muscles.

The cardiac prosthesis is formed from a biocompatible material. Suitable biocompatible materials include those known in the medical arts such as Dacron, Teflon, polyurethanes, nylons, polyesters, polyethylene, polypropylene, silastic, nitinol, nitinol mesh, titanium and titanium mesh or biologic membranes such as pericardium, pleura, peritoneum or duramater or tendon.

Suitable pericardial tissue can be obtained from equine, bovine, porcine, etc. sources, that has been treated as known in the art. The pericardium, for example, can be crosslinked with a cross linking agent such as glutaraldehyde or other non-aldehyde processes.

In one embodiment, the semi-circular band has a string with a needle of the appropriate size so that it can be passed around the bases of the papillary muscles. The whole band is threaded through the base of both papillary muscles followed by securing the extremity of the band that has the needle to the other extremity of the band so that the device becomes a closed ring. Alternatively, both extremities of the band have a portion of a tether. Once the band has been passed around the papillary muscles, the two tether portions are joined together with a knot, hook or securing means known in the art.

During surgery, the passage of the open semi-circular band though the base of both papillary muscles can be facilitated with a suitable instrument. This instrument is a long forceps or clamp with two arms with double curvature that is passed through the muscular bands that join the ventricular wall and the base of the papillary muscles. The open forceps grabs one of the extremities of the band and threads it through the base of the papillary muscles so that the semi-circular band surrounds both bases. The one or two tether portion(s), such as two strings, are then joined together.

Suitable instruments to achieve passage through the trabeculae include double curved vascular clamps, both right handed and left handed, and a Reverdin type suturing device, as well as others known in the art.

The degree of papillary muscle approximation is very important. The present studies have shown that in the normal mitral valve, the distance between tips of the papillary muscles is approximately equivalent to the intertrigonal distance. Therefore, since the normal intertrigonal distance of the individual patient is known with the described method based on the aortic valve annulus, the appropriate degree of papillary approximation to be achieved can be discerned. This papilloplasty can also be performed to relocate the displaced tricuspid papillary muscles.

Neo Basal Stay Chords

As above described, the two anterior stay chords (AS1 & AS2) play an important role to maintain not only the normal geometry of the mitral valve but also the left ventricular contractility. In congestive heart failure, the inextensible stay chords pull on the body of the anterior mitral leaflet distorting it and resulting in mitral regurgitation. The posterior stay chords (PS1 & PS2) may also be important for maintaining the normal geometry of the mitral valve.

The present invention provides the discovery that the distance between tips of papillary muscles and the mitral annulus is constant. Therefore, the present invention includes restoring the correct distance between papillary muscle and the mitral annulus and particularly between papillary muscles and right and left trigones (M1-T1 & M2-T2). This is achieved with four "neo-stay" chords. Commercially available sutures such as polypropylene or polytetrafluoroethylene are suitable as "neo-stay" chords and can be used to connect both papillary muscles to the trigones anteriorly (M1-T1 & M2-T2) and to the posterior mitral annulus (M1-PS1 & M2-PS2). However, any other type of connecting member whether synthetic or biologic, rigid or flexible can be used for this purpose. In one embodiment, these neo-stay chords can have markers spaced every few millimeters so as to simplify the determination of the correct length of the neo chords.

The key to this part of the technique is to determine the appropriate length of the new (neo) anterior and posterior stay chords. Based on data (not shown), the present invention provides that there is a relationship between the length of the normal anterior and posterior stay chords and it is close to the mitral intertrigonal distance. Therefore, the length of the neo-stay chords should be the same as the intertrigonal distance. Each suture is passed through each papillary muscle or through the papilloplasty ring, and anchored at the right and left trigones and through the extremities of the annuloplasty band and tied over it. In another preferred embodiment, besides the two new anterior basal chords, two other sutures are passed from the papillary muscles to the posterior mitral annulus and band. Similar neo-chords can be used in the tricuspid position.

Sizer

In order to simplify the above surgical maneuvers, a sizer (an intertrigonal sizer) has been developed. This novel instrument is designed to indicate the correct selection of the mitral annuloplasty band, appropriate distance between papillary muscles and the length of the neo-stay chords. This sizer can be made of metal, alloys or a plastic and can be a single instrument that can vary its dimensions or consist of a disposable set of sizers of different dimensions. Basically, the sizer is a rectangle attached to a handle. This rectangle can be made as a wire or a solid surface that advantageously is transparent. If selected to be a set of different sizes each sizer should have its size embossed onto the sizer. The surgeon will select the appropriate sizer either by following the aortic valve annulus method described above or by trying several different sizes.

To determine the intertrigonal distance and therefore the size of the mitral annuloplasty ring, the sizer is introduced through the mitral orifice placing its most proximal horizontal part against the anterior mitral leaflet. Its extremities should correspond with both trigones, i.e. the proximal horizontal side of the rectangle corresponds to the intertrigonal distance. The sizer is then removed from the heart and the papilloplasty semi-circular band placed around the papillary muscles. Before converting the semi-circular band into a ring, the sizer is again introduced through the mitral orifice and its distal horizontal side of the rectangle is placed between the papillary muscles. This side of the rectangle indicates to the surgeon the degree of papillary approximation needed. Once the papilloplasty has been performed, the vertical sides of the rectangle are used to indicate to the surgeon the appropriate length of the neo chords.

The following Figures serve to define the invention. The Figures are not intended limiting, but illustrative of the various aspects of the present inventions.

FIG. 1 depicts an operator's view of the mitral valve in the closed position as seen from the open left atrium. Only the atrial aspect of the valve can be seen. As described above, all anterior structures are identified with the letter A and those posterior with the letter P.

Structures supported by the anterior papillary muscle and situated to the left of the operator, are identified with the numeral 1 and those supported by the posterior papillary muscle (and to the right of the operator) are identified with the numeral 2. The two papillary muscles are M1 (left) and M2 (right). The two fibrous trigones are T1 and T2. The anterior leaflet is divided into A1 and A2 according to the insertion of their chords into either papillary muscle (M1 or M2). The commissural areas are identified as C1 and C2. The two lateral scallops of the posterior leaflet are identified as P1 and P2. The mid scallop (PM) is divided again according to the origin of its chords from the papillary muscles into PM1 and PM2. All chords are identified by their origin from the papillary muscles and insertion into the corresponding leaflet.

Figure 2:
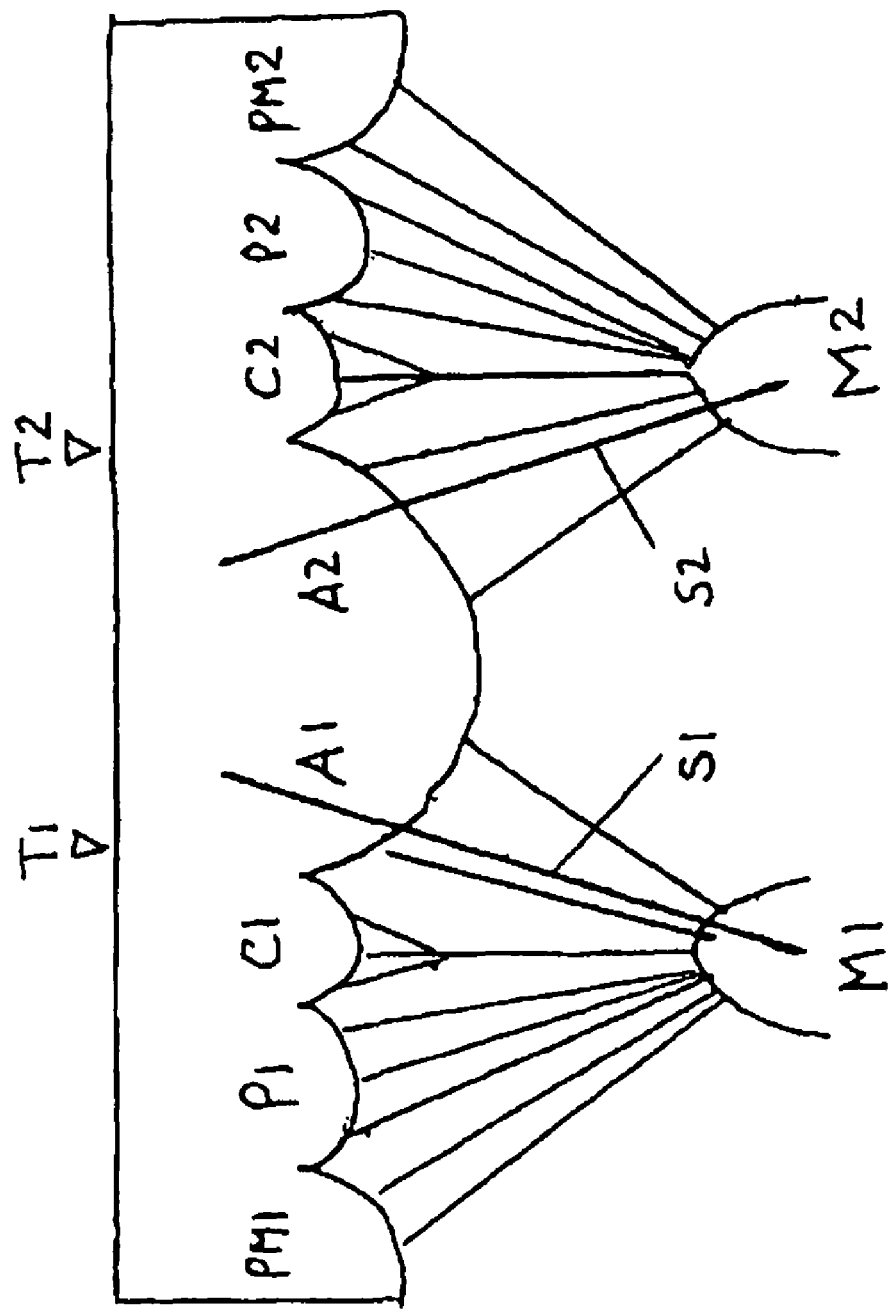
FIG. 2 represents the mitral valve opened through the center of the posterior leaflet showing leaflets, chordae tendineae and papillary muscles.

FIG. 2 provides an interior view of the mitral valve opened through the center of the posterior leaflet showing leaflets, chordae tendineae and papillary muscles. The terminology is used by practitioners to describe the different parts of the mitral valve. All structures connected to the anterior papillary muscle (M1) and situated to the left of the operator, carry the numeral 1 while those connected to the posterior papillary muscle (M2) are identified by the numeral 2. The anterior leaflet is therefore divided into A1 and A2 according to whether supported by chords from M1 or M2. The anterior leaflet is anchored to both fibrous trigones (T1 and T2). The posterior leaflet has three scallops termed P1, and P2 with a mid-scallop (PM) divided according to its chordal attachments intro PM1 and PM2.

Figure 3:
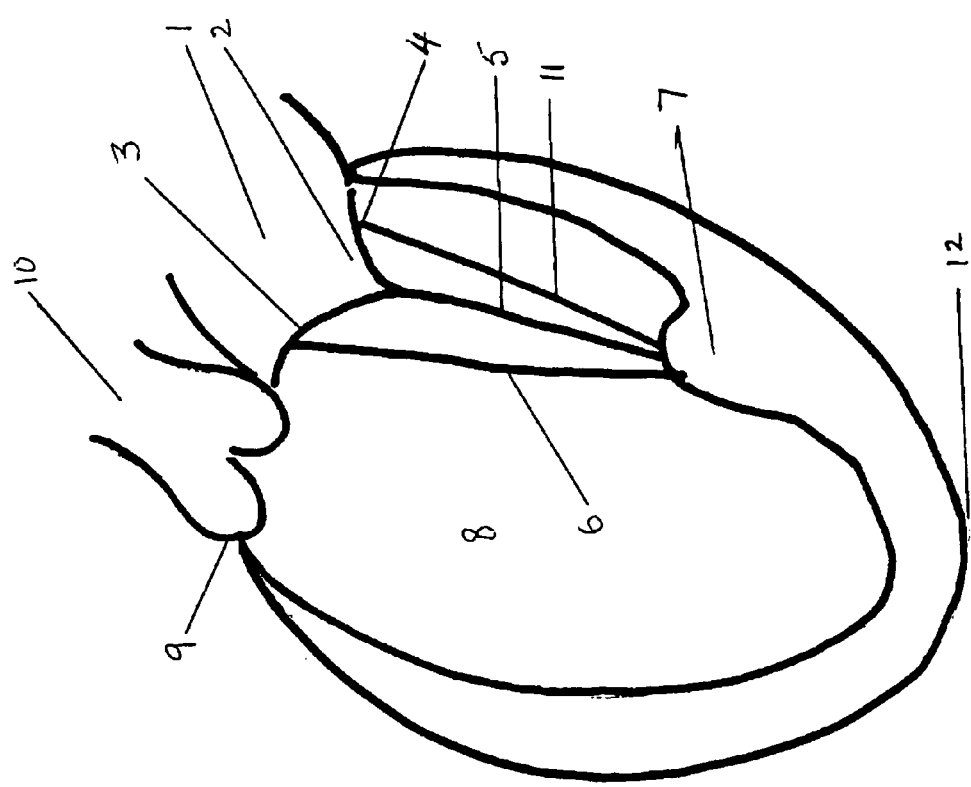
FIG. 3 is a longitudinal section of the left heart.

FIG. 3 depicts a longitudinal cross section of the left heart that includes the left atrium (1), the mitral valve (2), the anterior leaflet (3), the posterior leaflet (4), the marginal chord (5), the stay chord (6), the papillary muscle (7), the left ventricle (8), the aortic valve (9), the ascending aorta (10), the posterior stay chord (11), and the left ventricular apex (12).

Figure 4:
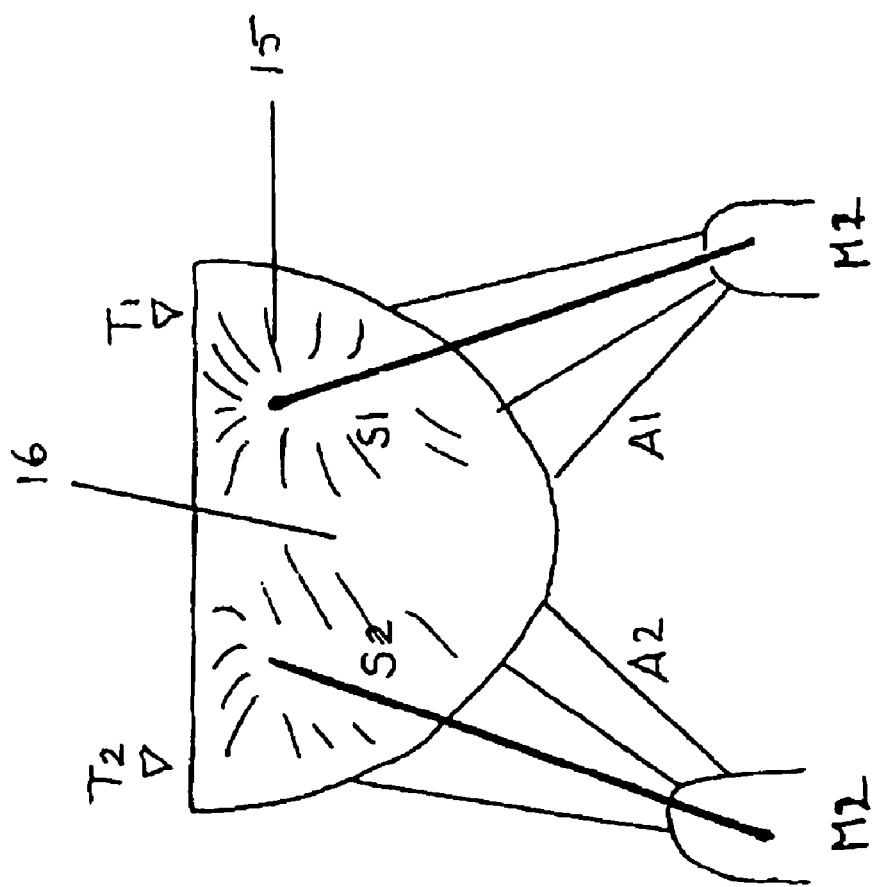
FIG. 4 shows of the direction of collagen fibers in the anterior mitral leaflet seen from the ventricular aspect.

FIG. 4 shows the direction of collagen fibers (15) in the anterior mitral leaflet (16) viewed from its ventricular aspect. T1: left fibrous trigone; T2: right fibrous trigone; S1 left stay chord; S2: right stay chord; A1: marginal chords to A1 leaflet; A2: marginal chords to A2 leaflet; M1 left papillary muscle; M2: right papillary muscle. Note how the collagen fibers of the anterior mitral leaflet radiate from the point of insertion of the stay chords (modified from Cochran et al. 5).

Figure 5:
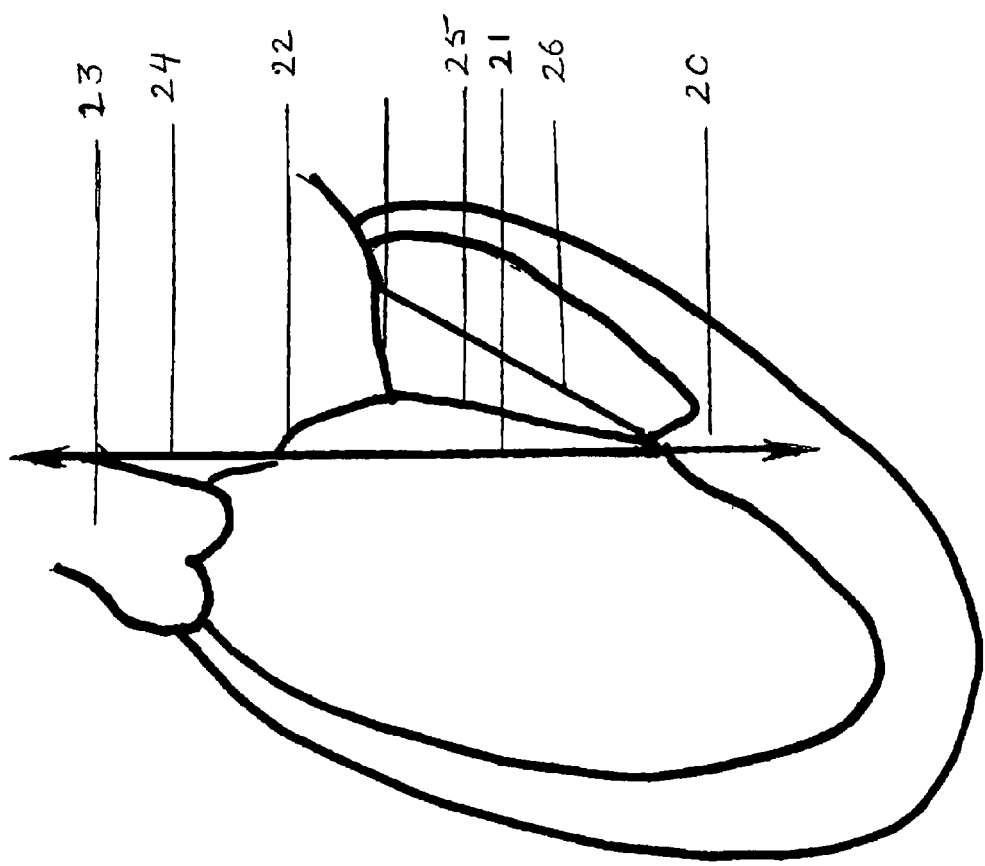
FIG. 5 is a longitudinal section of the left heart as in FIG. 3.

FIG. 5 diagrammatically shows the longitudinal section of the left heart as in FIG. 3. The papillary muscle (20), anterior stay chord (21), anterior leaflet (22) and aorta (23) are situated generally in a straight line (arrow 24). Marginal chord (25); Posterior stay chord (26). All these elements constitute the central structure of the cardiac pump.

Figure 6:
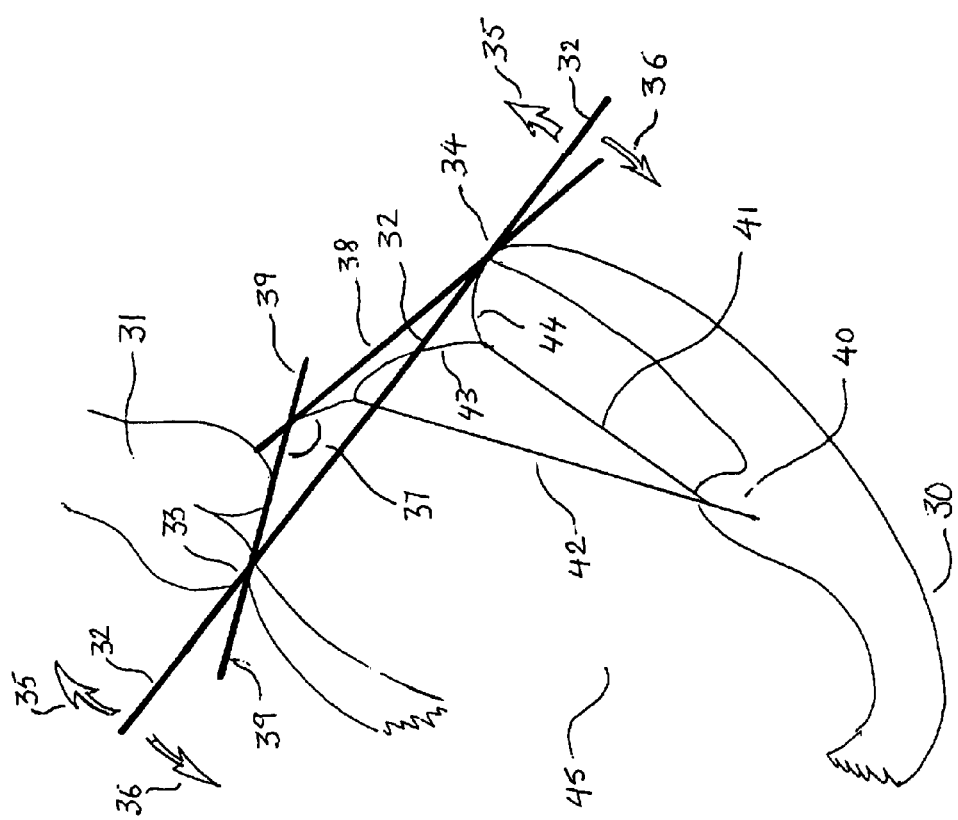
FIG. 6 is a longitudinal section of the left heart as in FIGS. 3 & 5. The apex and the ascending aorta are fixed and practically do not move during the cardiac cycle.

FIG. 6 is a diagram of a longitudinal section of the left heart as in FIGS. 3 & 5. The apex (30) and the ascending aorta (31) are fixed and practically do not move during the cardiac cycle. The atrioventricular plane (32) stretching between the base of the aortic valve (33) and the lateral aspect of the mitral annulus (34) moves up (diastole: arrow 35) and down (systole: arrow 36) during the cardiac cycle. The mitro-aortic angle (37) is formed by the plane of the mitral valve annulus (38) and the aortic valve plane (39). In the normal individual this angle practically does not change during the cardiac cycle.

Figure 7:
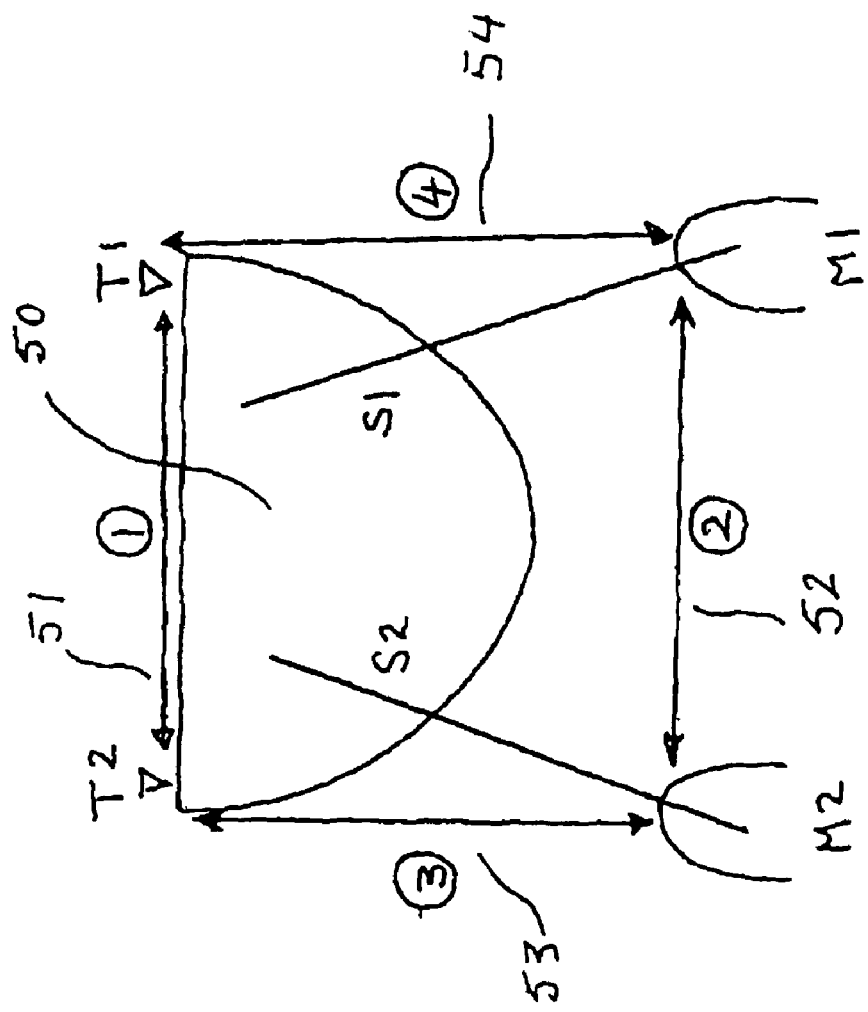
FIG. 7 is a depiction of the anterior mitral leaflet as seen from the left ventricle.

FIG. 7 is a diagram of the anterior mitral leaflet (50) as seen from the left ventricle. The left (T1) fibrous trigone and right (T2) fibrous trigone, left (S1) stay chord and right (S2) stay chord and left (M1) papillary muscle and right (M2) papillary muscle are shown. The intertrigonal distance T1-T2 (51) is essentially equivalent to the inter-papillary muscle (M1-M2) distance (52). The distances (53) and (54) between papillary muscles and trigones (M1-T1 and M2-T2) are essentially equivalent to the intertrigonal distance (51). For practical purposes, once the intertrigonal distance is determined, the other distances are known.

Figure 8:
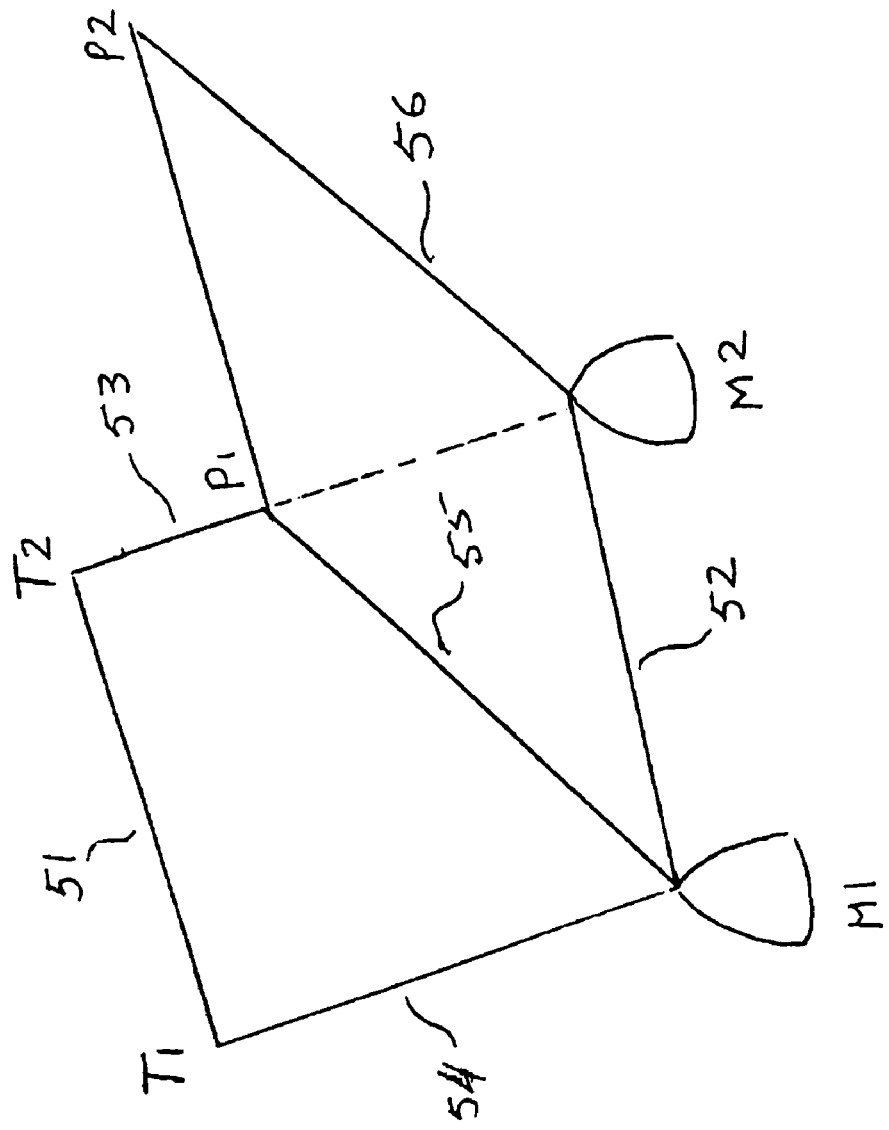
FIG. 8 is the basic geometry of the mitral apparatus.

FIG. 8 depicts the basic geometry of the mitral apparatus which supports the methods of the present invention. All distances between the key elements of the mitral valve are similar. Based on the intertrigonal distance (51) the interpapillary distance (52), papillary muscles to trigones (53 & 54); and papillary muscles to the posterior mitral annulus at the level of the mid-scallop clefts (55 & 56) are known.

Figure 9:
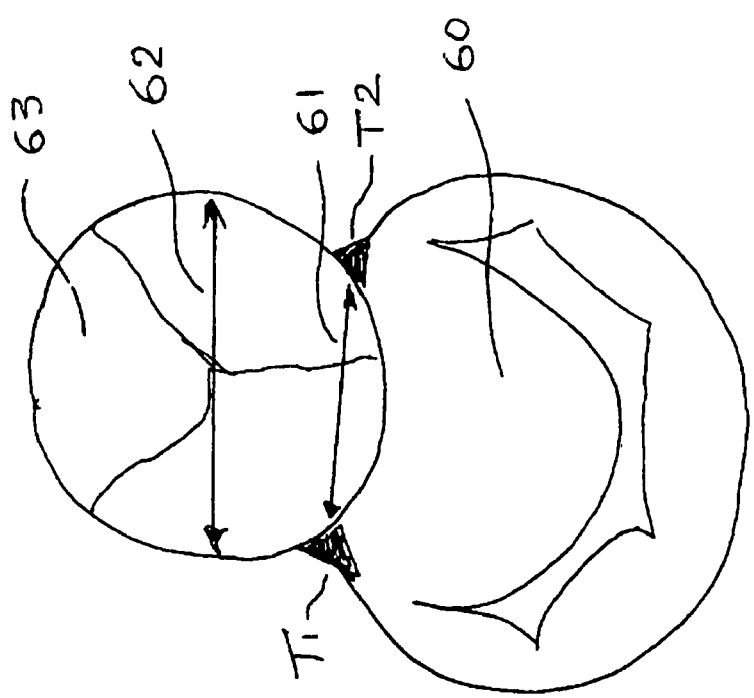
FIG. 9 pertains to a method for determining the mitral intertrigonal distance (T1-T2) derived from the diameter of the annulus of the aortic valve.

FIG. 9 is a graphical representation of a method for determining the mitral (60) intertrigonal distance (61: T1-T2) derived from the diameter of the annulus of the aortic valve (62). The method is based on the anatomic distinction that the left (T1) trigone and right (T2) trigone are common to the aortic valve (63) and mitral (60) valve. While the intertrigonal distance (61) (T1-T2) cannot generally be obtained by echocardiography, the diameter of the aortic valve base (62) is accurately obtained with echocardiography. The intertrigonal distance (61: T1-T2) can be obtained by dividing the aortic base diameter (62) by 0.8. This distance forms the base for determining the normal relationships in a healthy individual between papillary muscles, stay chords and mitral annulus.

Figure 10:
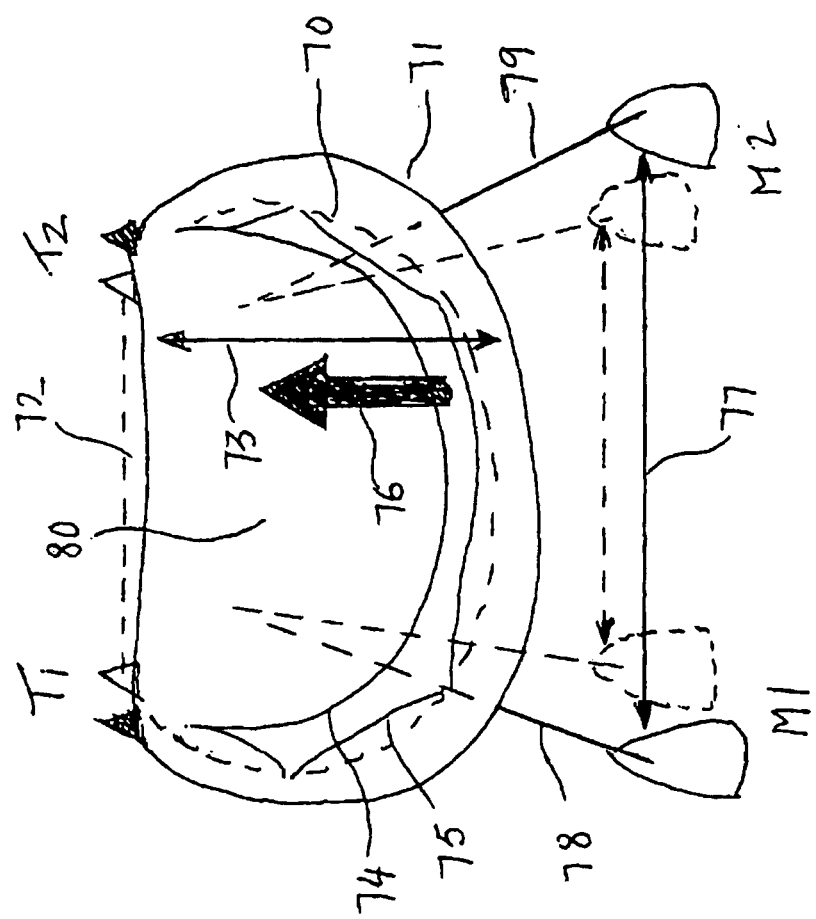
FIG. 10 demonstrates the geometrical changes present in heart failure. The normal mitral annulus (dotted line) dilates particularly in its posterior (shown as a continuous line).

FIG. 10 is a simplified diagram showing the geometrical changes present in heart failure. The normal mitral annulus (70) (dotted line) dilates particularly in its posterior part (71) (shown as a continuous line). Both the intertrigonal distance (72) and the anteroposterior mitral diameter (73) increase separating the anterior (74) mitral leaflet from the posterior (75) mitral leaflet inducing valve regurgitation (arrow 76). Also, the papillary muscles (M1 & M2) are displaced away from each other (relative to a healthy heart) increasing the interpapillary distance (77). This papillary muscle separation pulls on both anterior stay chords S1 & S2 (78 & 79) that pull further the anterior mitral leaflet (80) towards the ventricle reducing its mobility and increasing the regurgitation (arrow 76).

Figure 11:
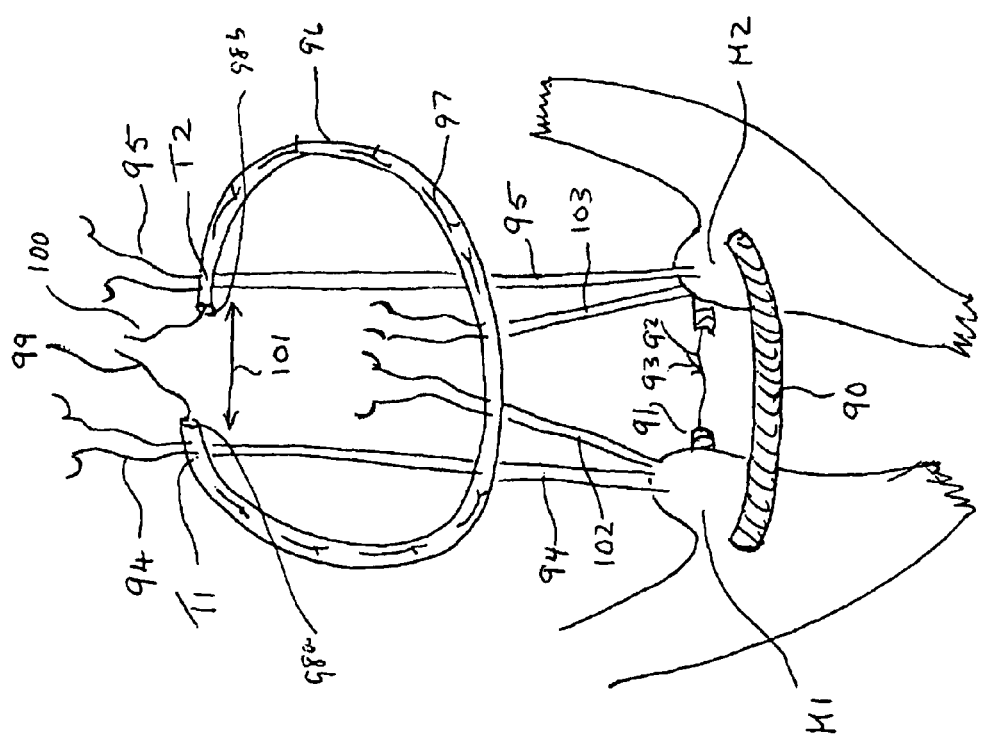
FIG. 11 provides a surgical system to restore the central structure of the cardiac pump in three different steps.

FIG. 11 is a simplified diagram of the surgical system to restore the central structure of the cardiac pump. The present invention consists of three different steps and prostheses:

Step 1. Papilloplasty: the two papillary muscles (M1-M2) are approximated by threading the papilloplasty semi-circular band (90) through the base of the papillary muscles (M1 & M2). The tether, (in this example, two strings (91 & 92)) located at the extremities of the semi-circular band (90) are then joined together (93) converting the semi-circular band (90) into a complete ring.

Step 2: Restoring the normal continuity between the papillary muscles (M1 & M2) and the mitral annulus. Two double armed sutures (94 & 95; neo-stay chords) are anchored to both papillary muscles (M1 & M2) and passed from the ventricular to the atrial aspect of the mitral annulus at the level of the fibrous trigones (T1 & T2) and kept with a mosquito. Optionally, pledgets can be incorporated about the muscle and/or trigone tissue to help support the sutures.

Step 3: A mitral annuloplasty semi-circular band (96) of an appropriate size is sutured to the patient's mitral annulus with interrupted sutures (97) following techniques known in the art. Both extremities (98a & 98b) of the annuloplasty band (96) are anchored to both trigones (T1 and T2). Two anterior neo-stay chords (94 & 95) are then passed through the distal portions (98a & 98b) of the annuloplasty band (96). Two posterior neo-stay chords (102 & 103) are similarly passed from both papillary muscles (M1 & M2) to the band (96) at a level corresponding to the base of the clefts of the mid-scallop of the posterior leaflet. The two tether portions, for example strings, (99 & 100) of the annuloplasty band (96) are then joined so that the calculated intertrigonal distance (101) is achieved. A variety of methods to join the tethers (99 & 100) are contemplated in the present invention.

Figure 12A:
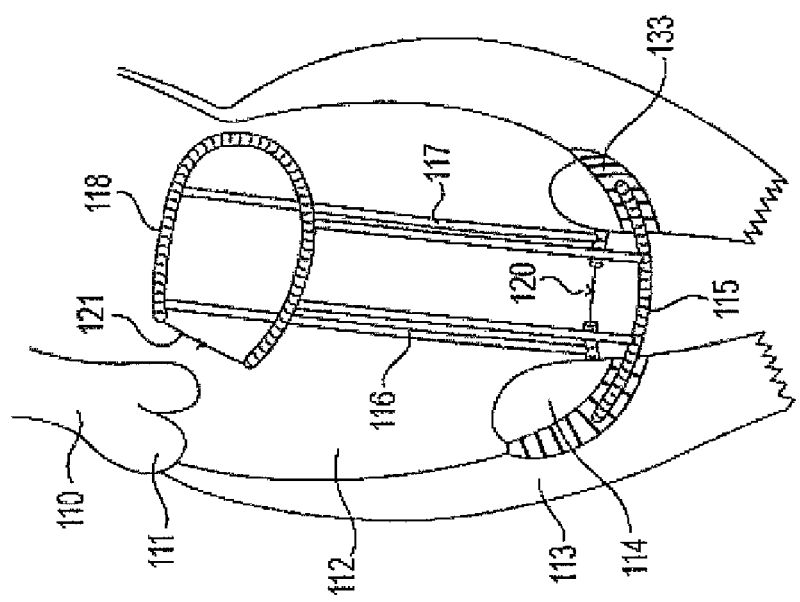
FIG. 12 is a simplified diagram for one aspect of the present invention, designed to the complete geometric reconstruction of the mitral valve in patients with congestive heart failure and mitral regurgitation.
Figure 12B:
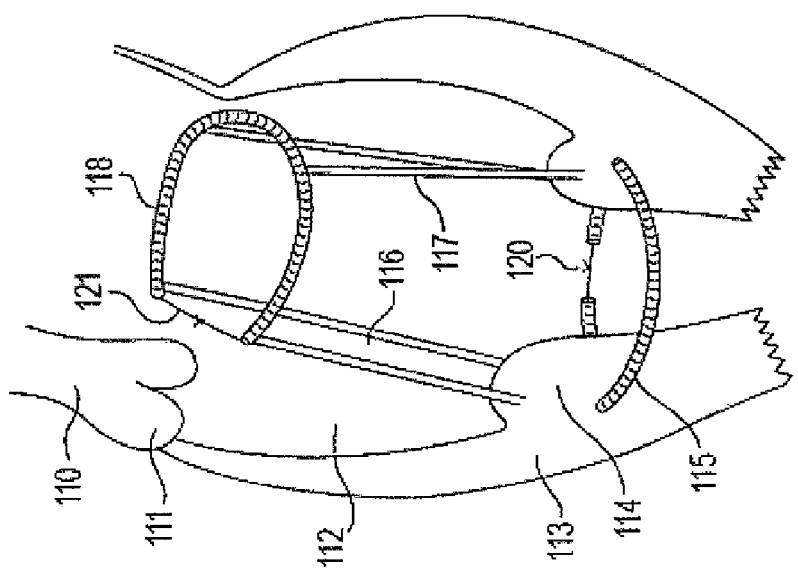

FIG. 12A is a simplified diagram depicting one aspect of the present invention, designed for geometric reconstruction of the mitral valve in patients with congestive heart failure and/or mitral regurgitation: aortic root (110); aortic valve (111); left ventricular cavity (112); left ventricular wall (113); papillary muscle (114); Papilloplasty semi-circular band (115) with tether portion secured (120) to form a ring; anterior neo-stay chords (116); posterior neo-stay chords (117); mitral annuloplasty semi-circular band (118) with tether portion secured (121) to form a ring. FIG. 12B is the same as FIG. 12A clearly showing papilloplasty band (115) passed through trabeculae (133) and anterior neo-stay chords (116) and posterior neo-stay chords (117) connected to annuloplasty band (118) and papilloplasty band (133).

Figure 13:
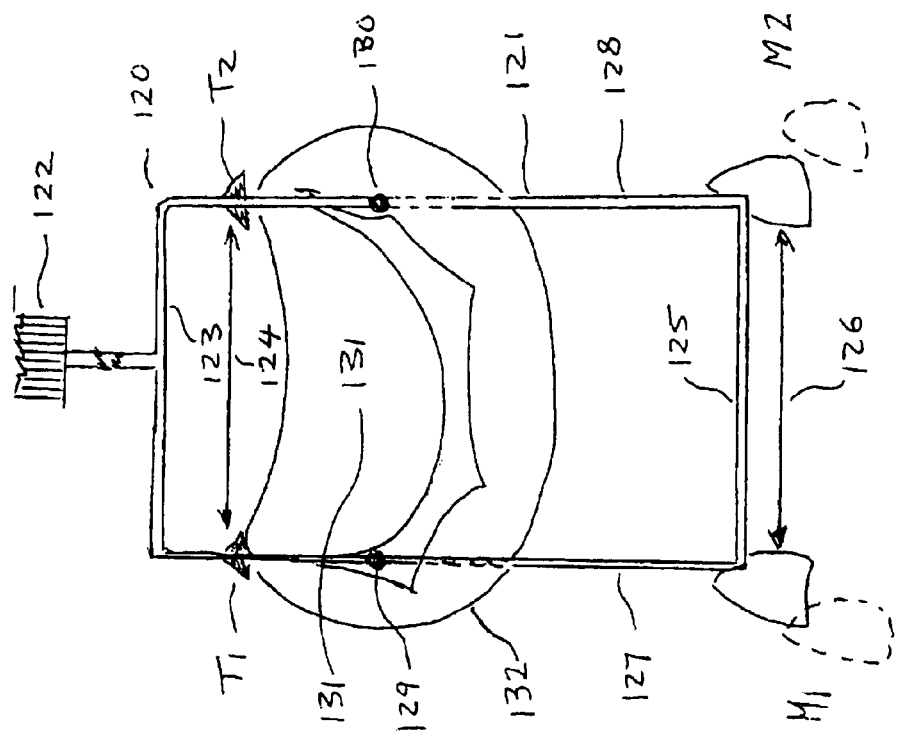
FIG. 13 depicts an instrument designed to facilitate the surgical maneuvers necessary to restore the central structure of the cardiac pump.

FIG. 13 shows one aspect of an instrument designed to facilitate the surgical maneuvers necessary to restore the central structure of the cardiac pump. The instrument (120) generally includes a rectangular frame (121), e.g., wire, held with a handle (122). The proximal or upper, horizontal portion of the frame (123) is slightly curved and is designed to determine the theoretical normal intertrigonal distance (T1-T2; 124) of the patient. The distal or lower horizontal side o the rectangle (125) is designed to indicate the desired distance between papillary muscles M1-M2 (126). The vertical sides of the rectangle (127 & 128) are designed to assist the operator in determining the appropriate length of the neo-stay chords. Two markers (129 & 130) are located in the vertical sides (127 & 128) of the rectangle. The distance between the markers (129 & 130) and the horizontal distal side (125) of the rectangle (121) is equal to the intertrigonal distance (124: T1-T2).

The sizer is introduced by the operator through the mitral orifice and placed against the anterior mitral leaflet (131). The distal portion (125) is placed between the two papillary muscles (M1 & M2) indicating the desired distance of papillary muscle to be achieved with the papilloplasty (dotted line: position of papillary muscles in patient; continuous line: intended new location of the papillary muscles). Once the papilloplasty has been performed, the sizer is reintroduced through the mitral orifice and the markers (129 & 130) of the instrument (120) are placed at the level of the trigones T1 & T2. The anterior and posterior neo-stay chords (already passed through the papillary muscles M1 & M2 and mitral annulus (132) are tied against the mitral annuloplasty ring so that their length is similar to the intertrigonal distance (123).

FIG. 14 depicts color coded suture to be used as neo-stay chords. FIG. 14a provides a suture that helps the operator in determining the correct length of the neo-stay chords. The suture (140) can include needles at each extremity (141 & 142) i.e. a "double ended suture" and is marked every 5-10 mm with alternating colors (143). Alternatively, FIG. 14b depicts an embodiment where the middle segment (143) of the suture (144) is marked with a different color with the length varying between about 50 mm and 120 mm (145).

Figure 15:
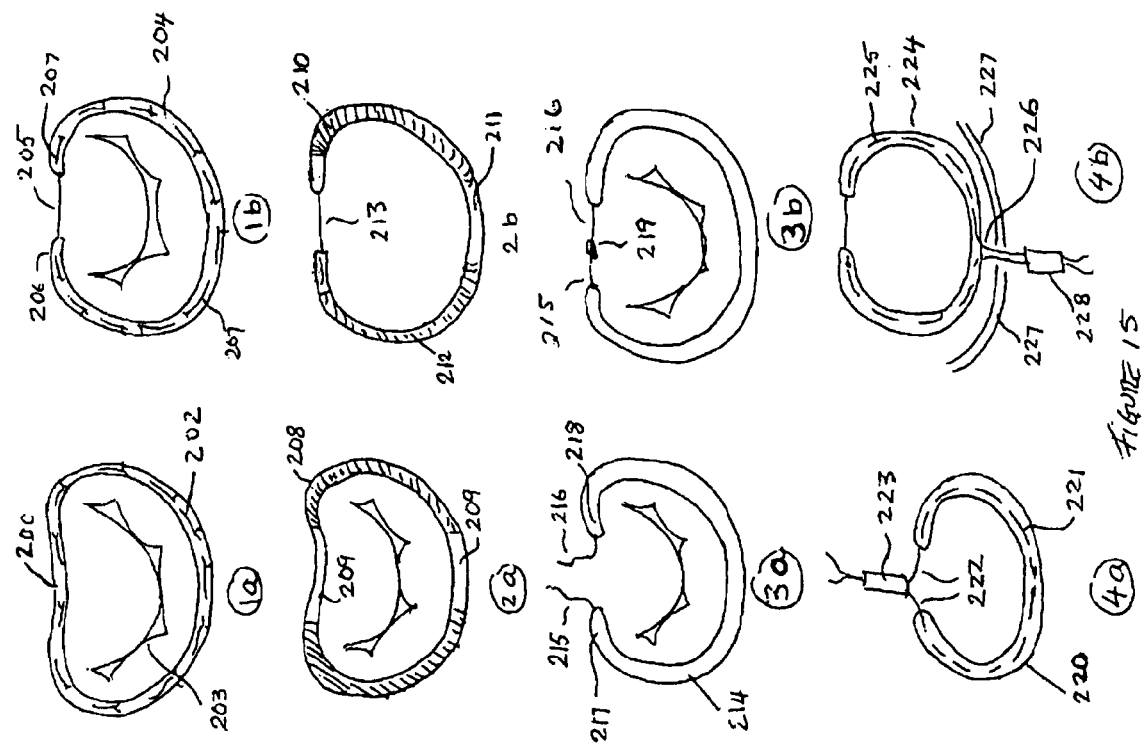
FIG. 15 provides diagrams of different mitral or tricuspid annuloplasty and semi-circular bands for ischemic and dilated cardiomyopathies.

FIG. 15 provides various diagrams of different mitral or tricuspid annuloplasty rings and semi-circular bands for ischemic and dilated cardiomyopathies. For example, the diagrams show the different types of bands/rings sutured to the mitral valve annulus. However, it should be understood that 1b, 2b, 3a, 3b, 4a and 4b can also be used as a papillary (cardiac) semi-circular muscle bands as described throughout the specification.

1a: Standard Complete Medtronic Duran Flexible Ring. The ring (200) has been sutured with interrupted sutures (202) to the annulus of the mitral valve (203). 1b: Semi-circular band (204) of the present invention. The band (204) has a tether, i.e., a string (205) that joins the extremities (206 & 207) of the band (204) making it a complete ring. The band (204) has been sutured to the posterior mitral annulus and the distal portions (206 & 207) of the band (204) are anchored to the trigones (T1 & T2).

Ring (2a) and semi-circular band (2b) with alternating rigid or semirigid (208) and flexible (209) components. The location and lengths of the rigid (208) and flexible (209) segments can be varied according to specific needs. In 2b the same construction with rigid (210) and flexible (211) segments is applied to the band (212) with tether (213).

3a: Semi-circular flexible band (3a) with tether portions, i.e., strings (215 & 216) anchored to the distal aspects (217 and 218) of the semi-circular band (214). 3b: The two tether portions (215 & 216) have been joined together (219) making the semi-circular band into a ring. A variety of methods to join tethers (215 & 216) are known in the art.

4a: The flexible semi-circular band (220) includes a running suture along its length (221) which is longer than the band (220). Distal portions of the suture (222) are passed through a tourniquet (223) which allows for the reduction of the whole length of the mitral annulus. 4b: The flexible semi-circular band (224) has a running suture (225). Distal portions of the suture (225) are exteriorized from the band (224) at selected levels of the band corresponding to the posterior annuls (226). In one example, the distal ends of the suture (225) are then exteriorized through the wall of the left atrium (227) and passed through a tourniquet (228). This design allows for the regulation of the annuloplasty size from outside of the heart after normal heart beat has been restored. Under echocardiographic control the annuloplasty can be tightened until the mitral regurgitation has disappeared.

Figure 16:
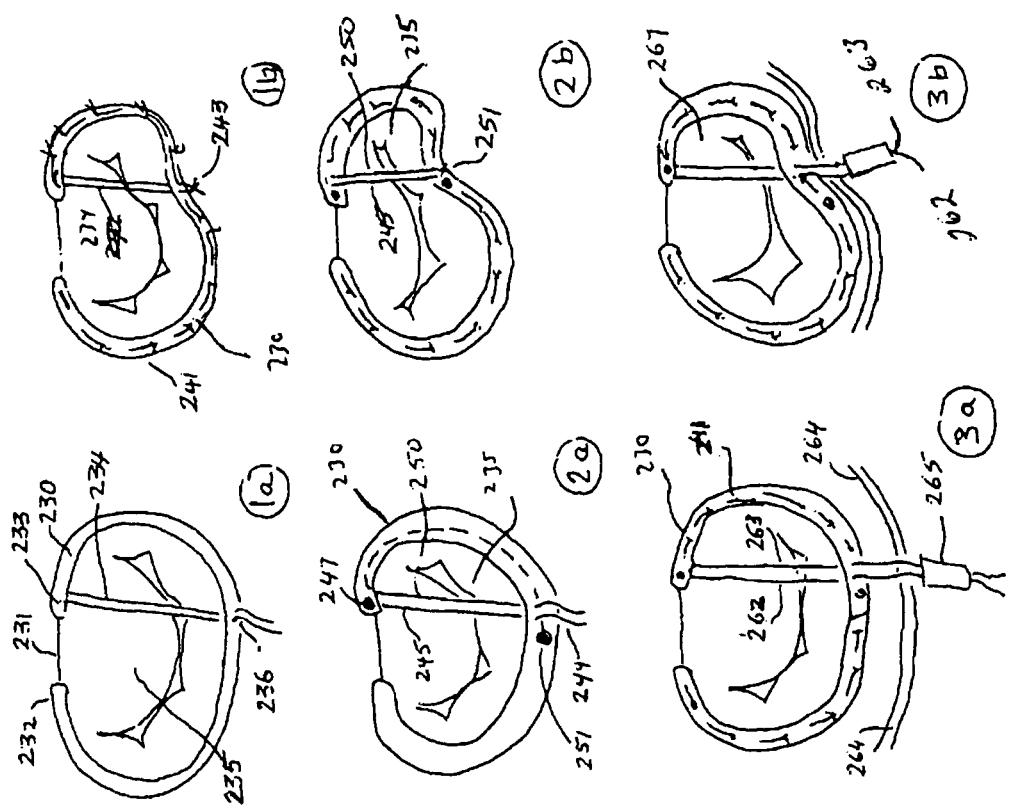
FIG. 16 depicts diagrams of different alternatives to selectively deform an annuloplasty ring and consequently the mitral or tricuspid annulus.

FIG. 16 depicts diagrams of different alternatives to selectively deform an annuloplasty ring and consequently the mitral or tricuspid annulus. For example, in ischemic mitral regurgitation the mitral annulus is enlarged non homogeneously. The antero-posterior diameter is often selectively enlarged. The following devices are directed towards the selective reduction of the antero-posterior diameter.

1a: The flexible semi-circular band (230) and string (231) sutured to the mitral annulus and trigones (232 & 233) has a second pair of strings (234) that are anchored to the band (230) at the level of its right extremity (233). The string—a double ended suture (234) crosses the mitral orifice (235) and re-enters the band (230) at the level of the mitral annulus corresponding to the cleft between the posterior mid-scallop and the lateral leaflet (236).

1b. After the band (230) has been sutured to the patient's mitral annulus (241), the two arms of the string (234) are tied over the band (243). The length of the string induces a selective reduction of the antero-posterior diameter of the annuloplasty.

2a An alternative to the above device includes placement of two separate strings (245 and 250). One string (245) is anchored to the extremity of the semi-circular band (230) corresponding to the right trigone (247). This string (245) crosses the mitral orifice (235) and the semi-circular band (230) and is exteriorized at the selected point (249) of the band (230). The other string (250) anchored at the mid-point of the band (251) runs within the lateral portion of the semi-circular band (230) and is exteriorized close to the anchoring point of the other string (247). The string (250) crosses the mitral orifice (235) parallel to string (245), crosses the semi-circular band and is exteriorized close to the other string (249).

2b: Tightening (251) the two strings (245 & 250) reduces selectively the right area of the mitral orifice (235) which is known to be a source of ischemic mitral regurgitation.

3a. The device shown in 2a can be controlled in a beating heart under echocardiographic control. Once the semi-circular band (230) has been sutured in place (241), two strings (262 & 263) are passed through the left atrial wall (264) and a tourniquet (265).

3b: Tightening the strings (262 & 263) with tourniquet (265) will reduce selectively the lateral area (267) of the mitral orifice.

REFERENCES CITED IN THE SPECIFICATION

1. Robinson T F et al. The Heart as a Suction Pump. Scientific American 1986; 254 :84-91.
2. Kumar N et al. A revised terminology for recording surgical findings of the mitral valve. Journal Heart Valve Disease 1995; 4 :70-75.
3. van Rijk-Zwikker G L et al. Mitral Valve Anatomy and Morphology: Relevance to Mitral Valve Replacement and Valve Reconstruction. J Cardiac Surgery 1994; 9 (2Suppl): 255-261.
4. Otsuji Y et al. Insights from three-dimensional echocardiography into the mechanism of functional mitral regurgitation. Direct in vivo demonstration of altered leaflet tethering geometry. Circulation 1997:96; 1999-2008.
5. Cochran R P et al. Nondestructive analysis of mitral valve collagen fiber orientation. American Society for Artificial Internal Organs Transactions 1991; 37(3):M447-448.
6. Alan M, Rosenhamer G. Atrioventricular plane displacement and left ventricular function. Journal American Society Echocardiography 1992; 5:427-433.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

I claim:

1. A method for reconstruction of cardiac geometry comprising:

attaching an annuloplasty device to an annulus of a heart valve of a ventricle;
inserting a papilloplasty device through trabeculae of papillary muscles of the ventricle; and
connecting the annuloplasty device to the papilloplasty device to prevent the devices from moving away from each other after the respective attaching and inserting, wherein the annuloplasty device is connected to the papilloplasty device by at least two neo basal stay chords such that the chords pass through the valve trigones before being directly connected to the annuloplasty device.

2. The method of claim 1, wherein a ratio of about 0.8 is fixed between an aortic valve annulus diameter and an intertrigonal distance.

3. The method of claim 1, wherein the method fixes a substantially similar distance between papillary muscle tips, papillary muscles to mitral fibrous trigones and intertrigonal distance.

* * * * *